United States Patent
Koch et al.

(10) Patent No.: US 10,682,052 B2
(45) Date of Patent: Jun. 16, 2020

(54) METHOD AND DEVICE FOR EXPOSING AT LEAST ONE SECTIONAL FACE INSIDE A LIGHT SCATTERING OBJECT

(71) Applicants: Thorlabs GmbH, Dachau/München (DE); Medizinisches Laserzentrum Lübeck GmbH, Lübeck (DE)

(72) Inventors: Peter Koch, Lübeck (DE); Gesa Franke, Lübeck (DE); Hendrik Spahr, Lübeck (DE); Helge Sudkamp, Lübeck (DE); Gereon Hüttmann, Lübeck (DE); Dierck Hillmann, Lübeck (DE); Reginald Birngruber, Lübeck (DE)

(73) Assignees: Medizinisches Laserzentrum Luebeck GmbH (DE); Thorlabs GmbH (DE)

( * ) Notice: Subject to any disclaimer, the term of this patent is extended or adjusted under 35 U.S.C. 154(b) by 148 days.

(21) Appl. No.: 15/752,125

(22) PCT Filed: Aug. 9, 2016

(86) PCT No.: PCT/EP2016/068975
§ 371 (c)(1),
(2) Date: Feb. 12, 2018

(87) PCT Pub. No.: WO2017/029160
PCT Pub. Date: Feb. 23, 2017

(65) Prior Publication Data
US 2018/0235461 A1 Aug. 23, 2018

(30) Foreign Application Priority Data

Aug. 14, 2015 (DE) .................. 10 2015 113 465

(51) Int. Cl.
*A61B 3/10* (2006.01)
*G01B 9/02* (2006.01)
(Continued)

(52) U.S. Cl.
CPC ................ *A61B 3/102* (2013.01); *A61B 3/12* (2013.01); *A61B 5/0035* (2013.01);
(Continued)

(58) Field of Classification Search
CPC .. A61B 3/10; A61B 3/12; A61B 3/102; A61B 5/0073; A61B 5/0035;
(Continued)

(56) References Cited

U.S. PATENT DOCUMENTS 5,398,113 A * 3/1995 de Groot ............ G01B 11/2441
356/497
6,195,168 B1 * 2/2001 De Lega ............ G01B 11/2441
356/497
(Continued)

FOREIGN PATENT DOCUMENTS

DE 10 2006 015 387 A1 10/2007
WO 2009/111609 A2 11/2009

OTHER PUBLICATIONS

Kwan Jeong et al. —"Fourier-domain digital holographic optical coherence imaging of living tissues", Applied Optics, Optical Society of America, Washington, DC; US, vol. 46, No. 22, Jul. 6, 2007; pp. 4999-5008.
(Continued)

*Primary Examiner* — Jie Lei
(74) *Attorney, Agent, or Firm* — Wood, Phillips, Katz, Clark & Mortimer

(57) ABSTRACT

The invention relates to an interferometric method, in which the light scattered by an object is imaged onto an electronic camera, wherein a sample light component is assigned to scattering sites on a sectional face in the interior of the object. This sample light component can be separated from the contributions of the other sample light components by processing of the camera image and leads to a sectional
(Continued)

image. A particular advantage of the invention lies in the fact that multiple parallel sectional faces can be exposed sequentially at predetermined intervals from each other in the interior of the object. Such a sequence of sectional images can be used to calculate a solid model of the object.

16 Claims, 1 Drawing Sheet

(51) Int. Cl.
    *A61B 3/12*     (2006.01)
    *G03H 1/06*     (2006.01)
    *G03H 1/04*     (2006.01)
    *G01N 21/47*     (2006.01)
    *A61B 5/00*     (2006.01)

(52) U.S. Cl.
    CPC ........ *A61B 5/0066* (2013.01); *G01B 9/02032* (2013.01); *G01B 9/02047* (2013.01); *G01B 9/02054* (2013.01); *G01B 9/02077* (2013.01); *G01B 9/02082* (2013.01); *G01B 9/02084* (2013.01); *G01B 9/02091* (2013.01); *G01N 21/4795* (2013.01); *G03H 1/0443* (2013.01); *G03H 1/0465* (2013.01); *G03H 1/06* (2013.01); *A61B 5/0073* (2013.01); *G01N 2021/479* (2013.01); *G03H 2001/0445* (2013.01); *G03H 2001/0467* (2013.01); *G03H 2222/24* (2013.01); *G03H 2223/26* (2013.01)

(58) Field of Classification Search
    CPC .... A61B 5/0066; G01B 9/02; G01B 9/02084; G01B 9/02032; G01B 9/02047; G01B 9/02082; G01B 9/902054; G01B 9/02077; G01B 9/02091; G01N 21/4795; G01N 2021/479; G03H 1/0443; G03H 1/0465; G03H 1/06; G03H 2001/0445; G03H 2001/0467; G03H 2222/24; G03H 2223/26
    USPC ........ 351/206, 210, 221, 246; 600/476, 473; 356/450, 498, 513, 511
    See application file for complete search history.

(56) References Cited

U.S. PATENT DOCUMENTS

| | | | |
|---|---|---|---|
| 2004/0027576 A1* | 2/2004 | De Groot | G01B 11/2441 356/498 |
| 2010/0331672 A1 | 12/2010 | Nolte et al. | |
| 2015/0062592 A1 | 3/2015 | Nolte et al. | |

OTHER PUBLICATIONS

Dubois A. et al, —"Ultrahigh-resolution full-field optical coherence tomography", Applied Optics, Optical Society of America, Washington, DC; US, vol. 43, No. 14, May 10, 2004; pp. 2874-2883.

* cited by examiner

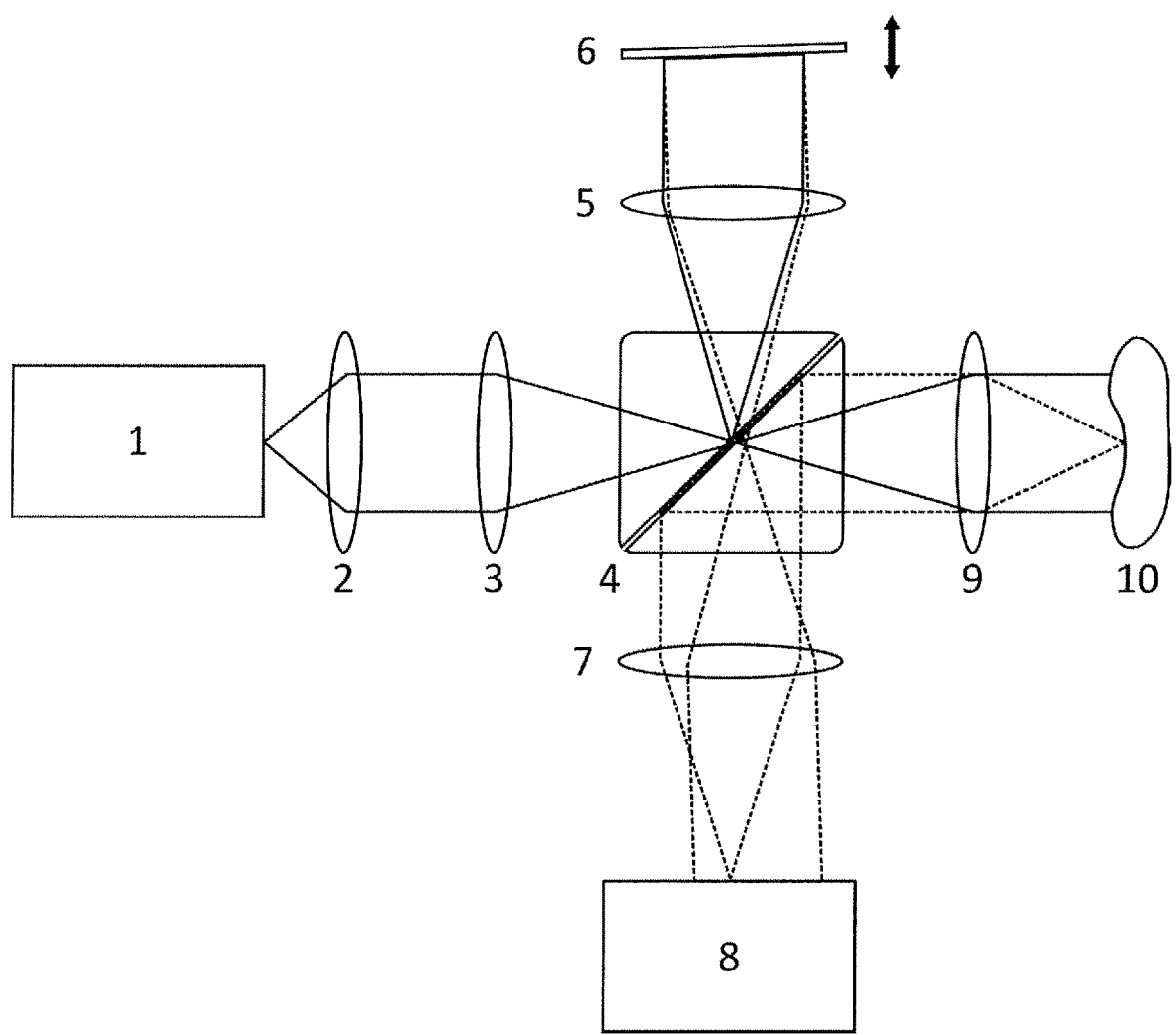

METHOD AND DEVICE FOR EXPOSING AT LEAST ONE SECTIONAL FACE INSIDE A LIGHT SCATTERING OBJECT

TECHNICAL FIELD OF THE INVENTION

The invention relates to a method and a device for exposing one or more sectional faces within a light scattering object. In the method, short coherent light can be split into a sample beam and a reference beam, the object illuminated with the sample beam and the light scattered by the object being caused to interfere with the reference beam on an electronic planar detector, in the following a camera. The invention therefore relates to a method of short-coherent or white-light interferometry and a device which implements this method.

TECHNICAL BACKGROUND OF THE INVENTION

This description uses the term "exposure" to refer to the detection of light, which is scattered at least in part by a scattering object and arrives at a camera under physical manipulation of the light. The manipulation comprises both the optical imaging of the object and the superposition of sample light and reference light in an interferometer.

Optical Coherence Tomography (OCT) is currently one of the most important diagnostic procedures in the field of ophthalmology. Since its market introduction in 1996 by Humphrey Instrument and Zeiss, its resolution and measuring speed have significantly increased. However, the device size, costs and operating principle have remained essentially unchanged. OCT systems have up to now been available only in hospitals and well-equipped doctors' surgeries.

For many ophthalmic symptoms, however, a close monitoring of the patient in relation to therapeutic effects is desirable. Examples of this are, in particular, the drug-based injection therapy of the moist form of age-related macular degeneration (AMD), but also other diseases such as diabetic macular oedema or retinal vein occlusions. The long-term monitoring of a therapy should include a frequent, if not daily, depth-resolved observation of the fundus of the eye, which is possible only using an OCT device. Because of the large numbers of potential patients (approximately 1.8 million AMD patients in Germany), this is problematic and also cost-intensive to implement, if the patient is often forced to visit places where OCT devices are available.

It would be desirable, therefore, to have a simple, easy-to-use and, above all, inexpensive OCT-device available, which patients can use at home by themselves.

To achieve this objective, it would be desirable to reduce the costs of the OCT device significantly, for example by a factor of 5-10. It would also be beneficial for achieving this goal if the use of the OCT equipment by untrained personnel were possible. In particular, it would be beneficial to compensate for motion-related artefacts, which occur during hand-held measurements by an elderly patient.

A "homecare" OCT device will typically acquire and save a sequence of electronic images of sectional faces of the retina. From these, the tissue structure can be reconstructed in the form of a tomogram. This results in a representation of the structures of the retina that is interpretable by the doctor.

The period of time in which the whole sequence is acquired and stored will be referred to in the following as the measurement duration. The measurement duration should not last more than a few seconds. Each individual image of the sequence is then acquired in a very much shorter time interval, which is referred to hereafter as the exposure time. The exposure time is the same as the integration time for the intensities on the image sensor of the camera. This is distinct from the readout time of the data from the camera. It corresponds to the time interval that is required to convert the electric charges accumulated in the pixels first into voltages and then into digital information. The readout time normally sets a limit on the frame rate of a camera.

In OCT two different motion artefacts must be distinguished. Both occur due to the movement of the object relative to the measuring device. Movements in a lateral or axial direction on a time scale in the order of magnitude of the measurement duration lead to changes in the geometric mapping of the measured structures over the course of the measurement. The result is a geometric distortion of the tomogram. The most likely cause of such distortion artefacts is the patient, who might not manage to hold the OCT device steady during the measuring period and hence to focus with the eye on a specific point.

On the other hand, an axial movement of the retina can additionally occur within the exposure time, which then leads to a phase shift of the OCT signal. In particular, it is possible for the signal to be completely obliterated if the object is displaced by half a wavelength in the axial direction during the exposure time. For the application of OCT in ophthalmology, exposure times of less than 200 microseconds must be achieved, in order to avoid this artefact as far as possible.

In addition, during an examination of the retina with a hand-held OCT device the distance from the equipment to the eye cannot be very well controlled. A hand-held OCT device should therefore have a measuring range of at least one centimetre to be able to reliably scan the retina of any given patient without further preparation.

For some years now, holography procedures have been developed to determine the scatterer distribution in diffusely scattering objects. These procedures use a tunable laser light source, i.e. spatially and temporally coherent light with variable wavelength, which splits the light into a sample beam and a reference beam and illuminates the object with the sample beam in a planar manner. The light returning from the object is either not imaged at all, or at infinity. A planar detector arranged in the sample beam thus measures in the far field of the object wave field. On the planar detector this wave field is superimposed with the reference beam, wherein the entire object depth contributes to interference effects due to the long coherence length of the laser light. The measurement result is actual a complex structured intensity pattern on the detector, which is stored as a hologram. A multiplicity of holograms is recorded at different wavelengths. The wave field of the reference beam is known in each case and in the subsequent evaluation in the computer is used to reconstruct the wave field of the sample beam on the detector from the holograms. This wave field can be propagated into any number of desired depths of the object, in order to determine the three-dimensional location of scattering centres.

Further details on procedures that use methods of digital holography (DH) can be obtained from the documents US 2008/137933 A1 and US 2014/092392 A1. In these procedures the currently achievable measurement depth is limited by the line width of the light source to a few millimetres. Any displacement of the object within the exposure time of the camera leads directly to a reduction in the contrast of the hologram. It changes the frequency or the phase angle of the measured sinusoidal modulation. This method is therefore susceptible to motion artefacts. Apart from the fact that a tunable laser light source is still not an inexpensive component, to provide motion compensation still further components for motion sensing, such as acceleration sensors, might be required.

The publication by Massatsch et al., ("Time-domain optical coherence tomography with digital holographic microscopy", Applied Optics, Vol. 44, No. 10, 1. April 2005) describes a holography method, in which a coherence window ("low coherence gating") is introduced to limit interferences on the camera from the outset to radiation from those depth layers, whose optical path length up to the camera matches the path length of the reference light within the coherence length. For a depth scan of the scattering object, the reference mirror is displaced, as is familiar from time domain (TD)-OCT. In this method, holograms are obtained which can be assigned to different depth planes of the object. The holograms allow the holographic reconstruction of the structural information of entire object planes. A pulsed laser with 80 femtosecond pulse duration is used as the light source here.

In the above holographic procedures, the images obtained are not directly interpretable, but require—generally compute-intensive—numerical analysis, to identify structures in spatial domain coordinates, i.e. an understandable model of the object.

Interestingly, a long-known device exists for the measurement of surface structures of diffusely scattering objects, whose structure is very similar to that of Massatsch et al. This is disclosed in DE 4 108 944 A1. Unlike in holography, here the surface is imaged on the camera, so that the spatial allocation of the structures using the incident light image obtained is straightforward. The surface profile of the object can be scanned by means of a movable reference mirror, wherein, in practice, the distance from the camera to the surface points scattering sample light, which contribute to interference with the reference light on the camera, is varied.

A disadvantage of the device of DE 4 108 944 A1 is the occurrence of speckle in the interference pattern, the phase angle of which is unknown a priori. The random intensities and phases of the speckle only permit conclusions as to the depth of the scattering object surface once this phase angle has been resolved by means of additional images. For this purpose, the reference mirror must be moved at each predetermined position at least once, so that the phase angle of all speckle changes. Due to this, in addition to the reference mirror designed with a drive for the rapid displacement of the mirror by the desired measurement depth in the object, which is in the order of magnitude of centimetres, either a phase modulator or a second drive with a positioning accuracy on the order of 10 nanometres is also required. This makes the device not only expensive, but likely also sensitive to vibrations and movements of all kinds. It appears unsuitable for a hand-held measuring device.

The document US 2009/12 0328 A1 describes a method for the detection of OCT signals by means of line sensors, which proposes a solution to prevent undersampling, even for large measuring depth intervals on the detector. In particular, it is shown there that by means of diffraction from a grating it is possible to change the propagation direction—and thus the phase front—of a light beam by an angle without at the same time tilting the coherence plane—also often referred to as the pulse front—along with it. The light beam propagating behind the grating in the direction of a diffraction plane maximum can have a path length distribution along its beam cross-section, which ensures that light from the left and right beam edge already no longer interfere with each other. Pulse front and phase front can be arranged at an angle to each other by means of diffraction.

SUMMARY OF THE INVENTION

The object of the invention is to propose a method for exposing at least one sectional face in the interior of a light scattering object, which can be performed quickly and with the most inexpensive components, and a device, which enables the application of the method by untrained users.

The object is achieved by means of the subject matter of the independent claims. Advantageous embodiments of the invention are the subject matter of the dependent claims.

One aspect of the invention is that the sample light scattered from the object is imaged on an electronic camera, wherein a sample light component can be assigned to scattering sites on a sectional face in the interior of the object. This sample light component can be separated from the contributions of the other sample light components by a processing of the camera image and leads to an image of the sectional face, i.e. a sectional image.

A further aspect of the invention consists in the fact that the shape, orientation and depth of an exposed sectional face can be defined by the user.

A further aspect of the invention is the fact that multiple parallel sectional faces can be exposed sequentially at predetermined intervals from each other in the interior of the object. Such a sequence of sectional images can be used to calculate a solid model of the object.

A further aspect of the invention consists in the application of the method for the exposure of the live retina. A particularly advantageous aspect of this is the possibility of detection and compensation of relative movements of the retina relative to the camera during the acquisition of a sequence of camera images directly from the image data. This allows the implementation of the invention in a hand-held measuring device.

An exemplary embodiment of the invention relates to a method for exposing a sectional face in the interior of a light scattering object. The method comprises the steps:

provision of a light source, which emits the light with a predetermined central wavelength and a coherence length of less than 25 microns;

division of the light from the light source into sample light and reference light;

surface illumination of the object with the sample light;

imaging of the sample light scattered from the object on an electronic camera with pixels of pixel width P by configuring a mean speckle diameter D greater than two pixels wide along at least one axis in the camera plane;

causing reference and sample light to interfere on the camera, by configuring a path length profile and a phase gradient of the reference light along the predetermined axis in the camera plane, wherein the phase gradient has a contribution from the interval between $2\pi/D$ and $\pi/P$;

acquisition of a camera image, wherein only the sample light scattered by a sectional face in the interior of the object and having the path length profile of the reference light contributes to interference patterns.

An advantageous extension of the invention consists of the displacement of the path length profile of the reference beam with a time-dependent velocity and acquisition of further camera images, each at least indexed with a measure of the time-dependent displacement of the path length profile.

Preferably, the invention is extended to include a processing step of separating a camera image into a sectional image and an incident light image based on the configured phase gradients.

A particularly advantageous design of the invention provides that a three-dimensional model of the object is calculated from a multiplicity of differently indexed camera images by the sectional image values being assigned to a voxel array, taking into account the relative displacement of images of identical structures in differently indexed incident light images.

In the application of the invention to the live retina as a scattering object in a particularly preferred configuration of the invention, from the relative displacement of the image of at least one layer boundary of the retina in differently indexed camera images, the change in the distance of the retina from the camera between the acquisition times of the camera images is inferred.

The invention allows a three-dimensional retina scan within a few seconds with an inexpensive and, if necessary, hand-held device.

BRIEF DESCRIPTION OF THE DRAWINGS

In the following, the invention is described in greater detail on the basis of exemplary embodiments and by reference to FIG. 1. This shows:

FIG. 1 a sketch of a device in accordance with an embodiment of the invention.

DETAILED DESCRIPTION

It will first be explained what relevance the size of the speckle on the camera and the phase gradient have for the invention.

It is already known from DE 4 108 944 A1 that the sample light exhibits speckles, which can be problematic. In general, speckle effects occur in the illumination of scattering objects with at least partially coherent light, if the mean distance between the scattering centres is very much smaller than the dimensions of the resulting focussing volume. In the case of a large scatterer density, the components scattered at different particles of an object volume therefore interfere with each other, and in the imaging of the object volume on a camera, areas of similar intensity and phase angle are formed. The contrast between these speckles depends on the degree of coherence of the light source and on the optical structure. The intensity of the speckle varies according to a stochastic distribution. The variation in the phase relation is uniformly distributed between zero and $2\pi$.

The invention then provides that the imaging of the sample light scattered by the object be performed in such a way that the speckle areas along at least one axis in the camera plane have a mean diameter D, which is greater than two pixel-widths P of the camera. The axis can be freely selected by the user; the choice of either one of the two pixel coordinate axes is recommended.

The mean diameter of a speckle D on the camera can be defined in a known manner, because it corresponds to the diffraction-limited resolution, which depends on the central wavelength of the light source $\lambda_0$, the diameter of the aperture diaphragm B and the focal length of the lens f, or the numerical aperture NA:

$$D = \frac{2.43 * \lambda_0 * f}{B} = \frac{1.22 * \lambda_0}{NA}$$

From this it can be obtained that the numerical aperture can be configured sufficiently small to arrive at a speckle diameter according to the invention of D>2*P. The limitation of the numerical aperture can also be achieved by means of an additional aperture diaphragm, which is placed in the Fourier plane of the image of the object. Along the selected axis in the camera plane it is also possible to configure a smaller numerical aperture than in the perpendicular direction, by using an eccentric aperture diaphragm, preferably a rectangular aperture with different side lengths. In addition, it is also possible to provide an additional magnifying lens in the imaging optics in order to keep the speckle diameters greater than two pixels wide.

The axial size of a speckle corresponds to the convolution of the coherence function of the light source and the axial point spread function of the image. For numerical apertures and coherence lengths commonly used in OCT, the axial speckle size is primarily determined by the coherence length of the light source. These conditions also apply to the present invention.

Furthermore, the invention provides for manipulating the reference light in such a way that it has a phase gradient along the same axis as that mentioned above in the camera plane, i.e. its phase front will be tilted towards the camera plane. This is achieved by the choice of a plane of incidence and a non-zero angle of incidence of the reference beam relative to the normal to the camera plane. The plane of incidence should be selected in such a way that it intersects the camera plane along that predetermined axis for which the speckle-diameter according to the invention D>2*P is also the case. The angle of incidence determines the size of the phase gradient.

It is part of the teaching according to the invention that the phase of the reference light should change by less than $2*\pi$ divided by twice the pixel width of the camera and at the same time by more than $2*\pi$ divided by the mean diameter of a speckle along the predetermined axis.

The incident angle $\alpha$ of the reference beam with respect to the normal to the camera generates a fringe pattern on the camera plane along the line of intersection of the camera with the plane of incidence, if the reference and sample light interfere. The periodic length of the strips is given by:

$$l_{Fringe} = \frac{\lambda_0}{\sin\alpha}$$

In particular, it is convenient to be able to scan the fringe pattern with the camera, and therefore, the period length should be chosen greater than two pixel-widths P $$l_{Fringe} > 2*P$$

which is equivalent to the constraint that the phase gradient must be less than $\pi/P$. The speckles along the predetermined axis are, in turn, provided with at least one period length of the strip, if the phase gradient is greater than $2*\pi/D$.

$$D > l_{Fringe}$$

Then, the individual speckles have been provided with the modulation of the fringe pattern in such a way that the camera can also detect the fringe pattern in the individual speckles. The speckles are therefore amenable to the separation of the camera images by a processing method to be described in greater detail below. This is because both the speckles and the fringes of the fringe pattern only appear on the camera if the reference and sample light components on the camera pixels have the same path length and are thus coherent. If this is the case, the visible speckles can be assigned to the sectional images.

Viewed in another way, the ambiguity of the true scattering intensity resulting from the unknown phase difference of the speckle and reference wave can be resolved by means of the phase gradient within a single image recording, since for every speckle at least two phase-shifted measurement values of the same speckle can be detected on adjacent pixels of the camera.

In the following the definition of the exposed sectional face by the specification of a path length profile of the reference light on the camera pixels is explained in more detail.

When incident on the camera, the reference beam defines a path length profile on the pixels along the axis with the phase gradient. The sample light scattered by the object may possibly contain a component that corresponds exactly to this path length profile, and only this component then contributes to interference patterns in the camera image. The imaged object points, the scattered light of which has the said path length profile, lie on a sectional face inside the scattering object. Typically, the sectional face is a plane whose normal is tilted by the angle $\alpha$—the angle of incidence of the reference beam on the camera—towards the optical axis.

The path length profile on the camera is directly dependent on the path length distribution in the beam cross-section of the reference beam when the latter impinges on the camera plane. If the reference light is deflected via mirrors or prisms, so that it is incident at an angle, then phase fronts and pulse fronts of the light correspond, i.e. in the beam cross-section parallel to the phase front, the path length is the same everywhere. On the camera, however, a linear path length profile is formed which, for example, comprises a path length interval with an interval width of around 500 wavelengths $\lambda_0$, hence typically a few hundred microns. Strictly speaking, the path length profile on the camera is a function of the two pixel coordinates, but it varies here only along one axis, which is predefined by the plane of incidence of the reference light.

The light from any given object point is focused into a camera pixel and undergoes interference with the reference light if the optical distance of the object point from the camera corresponds exactly to the value of the path length profile present on this pixel. Then, and only then, is the object point located in the sectional face. Therefore, the interference-capable sample light components in a camera image usually originate from different object depths, i.e., the sectional face that is imaged is inclined with respect to the optical axis. The location of the sectional face is generally determined by the path length profile on the camera.

It is also possible though, by diffraction at a suitable grating, as already mentioned in the prior art, to adjust the path length profile of the reference light in spite of the angled incidence of light on the camera, such that on all pixels, for example, the same path length exists. In this case, the sectional face is perpendicular to the optical axis of the image.

It should also be mentioned in passing that, even with spherical phase fronts and pulse fronts, i.e. with light from a point source, the objective is also achieved. The path length profile on the camera then has a more complex shape, however, so that the imaged sectional faces in the object are curved surfaces. In this description, solely for the purpose of simplification, it is assumed that the light is described by plane waves.

In any case, it should be emphasized that the path length profile of the reference light on the camera can be specified by the user. This profile defines which sectional face of the object—with regard to orientation, shape and distance from the camera—can then contribute to interference patterns in the acquired camera image.

The exposure according to the invention generates specially structured camera images. The structures of the images contain interference patterns, among other things, which are suitable for separating light components originating from predefined sectional faces from other light components. The invention can be understood as a method for generating rapid photographs of internal sectional faces of a light-scattering object with short coherence-coded location definition of the sectional faces ("Short-Coherence Interior Snapshot of Scattering Objects in Reflection", SCISSOR).

An actual representation of the sectional faces can be obtained from the camera image acquired with a very simple image processing, which is described below.

A particularly preferred extension of the invention consists of the displacement of the path length profile of the reference beam with a time-dependent velocity and acquisition of further camera images, each at least indexed with a measure of the time-dependent displacement of the path length profile. In this way, exposures of a plurality of sectional faces positioned parallel to each other inside the object are obtained.

In the simplest case, the displacement of the path length profile—this means that all path lengths on the camera pixels are changed by the same amount at the same time—is performed with a time-dependent speed, which has a rectangular progression. For example, all path lengths are increased monotonically with two alternating different speed values. During a time interval, in which the lower speed—e.g. with a value of zero—is present, the detection of a camera image occurs. The following camera image is acquired after at least one time interval at the higher speed has elapsed and the smaller speed is again present. The camera images thus expose parallel lying sectional faces, and the distance between these sectional faces is described by the displacement. It is also sufficient here to record a time index and to know the time-dependent speed, in order to calculate the displacement later.

The displacement of the path length profile on the camera can easily extend over a wide range of values on the order of centimetres. The particular sectional face being exposed is pushed through the object image by image, and from the totality of all camera images a fully reconstructable, three-dimensional record of the scattering intensity in the interior of the object is obtained, if the distance between adjacent sectional faces is chosen on the order of magnitude of the coherence length of the light source. The invention thus also allows the exposure of a solid portion of the scattering object.

For the embodiment of the invention, the following parameter ranges are recommended:

The central wavelength $\lambda_0$ is preferably chosen from the near to medium infrared spectrum, particularly preferably it is between 700 and 1500 nanometres.

The numerical aperture NA is preferably in the interval from 0.01 to 0.1. The numerical aperture particularly preferably has a value between 0.02 and 0.05.

The pixel width P of the camera is preferably in the interval from 0.5 to 20 microns. It is particularly preferably between 1 and 5 microns.

A single acquired camera image can preferably be separated by means of a two-dimensional Fourier filtering into a sectional image of the exposed sectional face and into an incident light image of the object. The collected light components, which must be assigned to the sectional image, are now provided with a periodic intensity modulation which is known in advance, which results from the phase gradient that is configured along the camera. Although these light components are characterized by speckle, the individual speckles also carry—clearly detectable by the camera—the said modulation. The modulation is described by a known two-dimensional wave number vector, also often referred to as the spatial frequency of the modulation.

A two-dimensional Fourier transform of a camera image results in particular in Fourier components in the vicinity of this spatial frequency. These Fourier components can be determined separately, then shifted by the spatial frequency of the phase gradient into the origin and transformed back into the spatial domain, in order to create a pictorial representation of only the sectional face, which has contributed to the interference in the camera image. The Fourier transformation of all the other Fourier components of the camera image leads to a conventional incident light image of the object, which shows no interference pattern from the superposition with the reference beam.

The term Fourier filtering is thus understood here to mean that a Fourier transformation is performed from the spatial domain into the wave number domain and back, in which predetermined Fourier coefficients are selected and separated. This approach to filtering frequency-based information is familiar to the person skilled in the art from the field of signal processing.

The above-described separation of a camera image into a sectional image and an incident light image by two-dimensional Fourier filtering of the acquired camera image with respect to the configured phase gradient automatically leads in an advantageous way to the result that detectable structures are registered jointly in the separated images. In particular, this means that all positions of structures in the incident light image can be applied for determining the position of structures in the sectional image.

This is particularly advantageous if it is desired to carry out the exposure of a solid object, such as the retina, with a hand-held SCISSOR system. To do so, a sequence of camera images for different sectional faces of the object must be acquired, to infer the three-dimensional distribution of the scattering intensities of the object from the sectional images. This distribution can be represented, for example, by a numerical voxel array as a model of the object, wherein the sectional image values—interpreted as the scattering intensities to be ascertained—are assigned to the three-dimensionally indexed voxels on a one-to-one basis.

Since the camera images are indexed with a measure of the displacement of the path length profile of the reference beam on the camera, with the image sequence one coordinate for the arrangement of the different sectional images in a voxel array is already available. But since the camera and object can move relative to each other during the measurement period—the acquisition of the entire image sequence—due to movements of the user or object, the sectional images can also be shifted relative to each other. In the absence of any user movement, however, the successively acquired incident light images are virtually identical. They show all the structures that would also be seen with a conventional camera. To automatically identify displacements of identical structures in electronic images, the prior art contains efficient algorithms, for example, matching can be performed in a Hough space using the displacement vector.

A particularly advantageous design of the invention therefore provides that a three-dimensional model of the object is calculated from a multiplicity of differently indexed camera images by the sectional image values being assigned to a voxel array, taking into account the relative displacement of images of identical structures in differently indexed incident light images. The production of such three-dimensional models, or voxel arrays, is advantageous for the simple reason that they allow the numerical calculation of other sectional images of any orientation through the object in a known manner.

If it is also known in advance that the object to be exposed has at least one scattering layer boundary with a known orientation to the optical axis—this is the case in particular for the live retina, where such boundaries are found between cell layers—then, it turns out to be unexpectedly advantageous if the sectional faces exposed according to the invention in the interior of the object are tilted towards the optical axis. This is because the sectional images show a clearly visible horizon, i.e., an image of the line of intersection between the sectional faces and the said scattering layer boundary, for all sectional faces for which this line of intersection exists. The horizon "moves" through the sectional images, if the displacement of the path length profile changes, in the sense that it can normally be seen in each sectional image at other pixel coordinates. The horizon additionally moves due to actual independent movements by the user, however.

The user movement between the recording of the camera images can be compensated as described, by means of the incident light images in the plane perpendicular to the optical axis, i.e. laterally. The third component of the user movement in the direction of the optical axis is normally inaccessible for OCT systems. But here, it can also be determined exactly, because after the compensation of the lateral movements of the user it is still possible to detect movements of the horizon if these originate from a change of the sectional face, which the user brings about by distance changes. Because the sectional faces are tilted with respect to the scattering layer boundary, the section line that is imaged then necessarily moves laterally and is thus captured by the camera. This means that, especially in retina measurement, it is possible from the relative displacement of the image in at least one layer boundary of the retina in differently indexed camera images, to infer the change in the distance of the retina from the camera between the acquisition times of the camera images.

It is therefore possible to obtain three-dimensional models of the scattering object in which user movements in three dimensions have been compensated, within the scope of the invention and without any additional measuring effort or sensors, but instead directly from the image data of the recorded camera images.

FIG. 1 shows the sketch of an exemplary SCISSOR device after the fashion of a Michelson interferometer.

Divergently emitted light from a temporally short-coherent light source (1) is first collimated by means of a collimator lens (2). A beam splitter (4) with a semi-transparent mirror is surrounded by four lenses (3, 5, 7, 9), which are arranged in such a way that firstly they illuminate the reference mirror (6) and the object (10) in each case with collimated light and secondly, also image the object (10) on the camera (8). The reference mirror (6) is tilted by a predefined angle $\alpha$, as a result of which the reflected reference beam is slightly laterally deflected and is incident on the plane of the electronic camera (8) at a slight angle. The light-scattering object (10) is arranged in the focal plane of the objective lens (9), wherein for clarity the numerical aperture is exaggerated in the sketch. In fact, all light-scattering points of the object (10) are imaged more or less sharply on the camera (8) regardless of their depth position within the object (10). The distance from the reference mirror (6) to the beam splitter (4) is varied by an actuator, not shown, —indicated by the double arrow in the sketch.

The angular interval for the angle α is calculated from the same considerations as above to $$M*D = M*\frac{1.22*\lambda_0}{NA} > \frac{\lambda_0}{\sin\alpha} > 2*P$$

Dividing the inequality by $\lambda_0$ and forming the reciprocal gives:

$$\frac{NA}{1.22*M} < \sin\alpha < \frac{\lambda_0}{2*P}$$

The magnification factor M is the ratio of image size to object size in the imaging. Here it is explicitly introduced to include the use of a magnifying lens in the imaging optics, for example, if too large an NA is selected. An important parameter for the invention is the speckle diameter on the camera, which here is given by M*D. Usually, it can be left at M=1.

For example, the allowable angular range for a is between 2.35° and 4.59° if the camera has pixels of pixel width 5 microns, a central wavelength of 800 nanometres is selected and the NA has the value of 0.05 commonly used in OCT. The angle interval will be greater for smaller numerical apertures and/or larger wavelengths. Only relatively large camera pixels are likely to require a magnification.

A SCISSOR device is always an interferometer device with a sample branch and a reference branch. In this case the sketch in FIG. 1 is only given as an exemplary embodiment of the device. For example, the reference light from the reference mirror (6) does not necessarily have to be passed through the beam splitter (4) and the lenses (5, 7) again, but could also bypass these components to reach the camera (8). Also, the tilted reference mirror (4) is only preferable, not mandatory. A required feature is a phase gradient on the camera (8), which is preferably generated simply by the angled incidence of the reference light. For example, the reference light could alternatively be laterally offset and passed perpendicular to the camera (8) through a diffraction grating, wherein the camera (8) is arranged at a location in the direction of a secondary diffraction maximum of the reference light. In this case, only a portion of the reference light is incident—but again under an angle—on the camera (8). The type of interferometer is also not restricted to the Michelson design.

Formulated more generally, it is an interferometer device for the exposure of a volume of a scattering object having a light source (1), which emits light with a coherence length less than 25 microns and central wavelength $\lambda_0$, a beam splitter (4) for dividing the light into a sample branch and a reference branch, means (5, 6) for changing the reference branch length, means (9) for surface illumination of the object (10) in the sample branch, an electronic camera (8) with pixels of width P, an imaging optical system (7, 9) with numerical aperture NA and magnification M arranged for imaging the light scattered by the object (10) onto the camera (8), and a computing unit for processing the acquired camera images, characterized in that the angle of incidence a of the light from the reference branch onto the camera is configured in accordance with the condition $\lambda_0/(2*P) > \sin(\alpha) > NA/(1.22*M)$.

An advantageous design of the device can consist of the imaging optical system (7, 9) comprising an eccentric aperture diaphragm, as explained above.

Preferably, the device has an actuator drive, which acts on the means (5, 6) for changing the reference branch length, and an actuator controller. The actuator controller is designed to be communicatively connected to the computing unit for processing the acquired images, to transfer to the computing unit data about the status of the reference branch, for example, its length and/or the speed of its length changes, at least maintaining the same rate as the image acquisition. Since the change in the reference branch length also causes the displacement of the path length profile of the reference beam on the camera (8), the computing unit can use the data from the actuator controller for indexing the camera images, for example, writing both together into the data memory of the camera (8).

Furthermore, the computing unit is preferably designed to calculate at least predetermined two-dimensional Fourier coefficients of the acquired camera images. It can thereby perform the separation of the recorded camera images into sectional images and incident light images and store them as separate images, for example in the electronic data store of the camera (8).

Alternatively however, the computing unit can also be limited to only verifying the presence of an evaluable sectional image in the camera image. For this purpose, it may be sufficient to calculate only Fourier components in the region of the already known spatial frequency of the phase gradient from the camera images and verify whether their absolute values exceed predefined threshold values. If this is not the case, then no evaluable sectional image has been acquired. The probable cause is that the reference branch length differs considerably from the distance from the object to the camera, so that no interference with the sample light is possible. Especially when measuring the retina of the living eye first, this case is initially likely when the device is held in front of the eye. The device must first find the location of the retina and adjust the reference branch to it. The computing unit can identify such a situation and in turn trigger the actuator to change the reference branch length in large steps, e.g. from several hundred microns up to millimetres, in order to accelerate the process of locating the object.

In any case, in a preferred design the computing unit is designed to identify Fourier coefficients of acquired camera images in step with the image acquisition and to compare them with predetermined threshold values, and to send predetermined commands to the actuator controller on the basis of the comparison result. This concept of feeding back the image acquisition and processing to the actuator controller also enables in particular a diagnosis-dependent variation of the change in the path length profile, therefore, the scanning speed across the sectional faces.

Preferably, the change in the path length profile of the reference beam occurs during a measurement in a monotonically ascending or descending manner over a range of at least one centimetre, particularly preferably 1 to 2 centimetres. It is within the scope of the invention to perform a plurality of measurements of the same object in immediate succession and also to use the results of a previous measurement for commands to the actuator controller in subsequent measurements.

For example, in the case of retina measurement, in a first measurement with a large increment of the change in the path length profile—e.g. by 100 microns—the position of the retina can be determined in a measuring window—for example of width 1-2 centimetres. Once the position of the retina is determined, the axial measuring range and the increment are then greatly reduced, for example by an order of magnitude in each case. The exact axial item of the measuring window can be adjusted to the previously measured position of the retina, and this is immediately followed by a second measurement with the reduced increment.

It must be emphasized here that the actuator can be very inexpensive, because it does not need to fulfil high technical demands. For example, the reference mirror (6) can be moved gradually, wherein it is stationary during an image acquisition by the camera. The actuator can also move the reference mirror (4) continuously while the camera (8) acquires a sequence of images. This is particularly advantageous, especially at high frame rates of the camera. In this case, the speed of the movement during the measurement period can be varied in a controlled manner by the actuator, either by software control according to specifications or by means of commands from the computing unit.

Inexpensive cameras available today can record, for example, around 800 images per second, i.e. one image every 1250 microseconds. For a complete scanning of a volume in the object in the sense of the sampling theorem, in this period of time the path length of the reference light should change by no more than half the coherence length, for example, typically around 7.5 microns. The maximum path length rate of change may then be given by $v_R$=6 mm/s, or in the above example, the reference mirror (6) may be displaced up to a maximum speed of 3 mm/s. Advantageously, the measurement period for a measurement range of e.g. 1.8 centimetres lasts no longer than 3 seconds.

If, however, the aim is to change the reference branch length continuously, i.e. also during the acquisition of individual camera images, then it is necessary to observe a sufficiently short exposure time, because all light components contributing to the interference will be cancelled out if the phase of the reference wave during the integration changes on all pixels of the camera (8) by $2\pi$, which is the case for a change in the path length profile about a central wavelength $\lambda_0$. Therefore, the exposure time must be configured to be less than $\lambda_0/v_R$. This allows the path length profile of the reference beam to be continuously displaced, wherein all path lengths vary by no more than a predetermined fraction of the central wavelength during an exposure time of the camera.

With the previous example values $\lambda_0$=800 nm and $v_R$=6 mm/s, an exposure time of less than about 133 microseconds must be provided. Preferably, the exposure time will be chosen to be shorter than $\lambda_0/(2*v_R)$, particularly preferably for example $\lambda_0/(4*v_R)$. In any case, the exposure time of less than 200 microseconds is suitable for avoiding short-term motion artefacts in the individual images.

Finally, if the measurement data from the device are collected at the user's home—or at any other place where the person who will analyse the data is not located—a preferred embodiment of the device is characterized by a data interface, which transmits the recorded and possibly processed images wirelessly, for example over WLAN or mobile radio networks, to predefined recipients preferably automatically. The receivers can be smartphones belonging to doctors or else servers on the Internet, which perform additional processing tasks and/or archiving processes. For example, tissue changes between two measurements of the retina can thus also be automatically translated into difference images and delivered to the doctor.

Essential advantages of a SCISSOR device are:

the device must be produced in a compact design with components fixed at the factory. The user does not have to perform any settings themselves. The reference branch length is varied automatically by a programmable control system. The position or the distance from the retina to the measuring device is not known a priori and also does not necessarily need to be determined absolutely during the measurement. Instead, the variation of the reference branch length can take place over such a large measuring range that the retina of the user is bound to be included in this measuring range.

The equipment can be held in front of the eye to be tested, either by the patient or nursing staff without prior OCT knowledge, provided it is held as still as possible.

The measurement only takes a few seconds, in which older patients should also be able to manage to hold the device steady. Movements of the user are additionally detected on the basis of the incident light images and can be compensated in a numerical modelling process.

The likely most expensive component of the SCISSOR device is the electronic camera, which should have as high a frame rate as possible. All other components are available at extremely low cost. The device should be available for sale in a price ange which is accessible for a private household.

A stored image sequence can be sent to the doctor via remote data transmission. It is preferably sent—if necessary in anonymised form—to a server on the Internet, which performs an automatic data processing. This can comprise, for example, the creation of a three-dimensional model of the retina with sectional images ordered by the doctor. In particular, the files can be archived. Furthermore, for follow-up checks this results in a facility to display changes in the scattering intensity distribution in the retina by comparison of the image sequences and/or models between at least two examination occasions.

The availability of a large number of retinal images and treatment progress records on the Internet can be useful for the purposes of medical research and teaching.

A SCISSOR device can also be used for both medical and safety-related objectives. This is due to the fact that the association of retina scans, in particular, to specific individuals is possible, and even intentional, and so their identity can be reliably biometrically verified on the basis of the unique and now also three-dimensionally recordable retina structures.

The invention claimed is:

1. A method for exposing a sectional face in the interior of a light scattering object, having the steps:
   providing a light source, which emits the light with a predetermined central wavelength and a coherence length of less than 25 microns;
   dividing the light from the light source into sample light and reference light;
   laminary illuminating the object with the sample light;
   feeding the sample light scattered from the object to an electronic camera with pixels of pixel width P;
   wherein the light scattered from the object is fed to the electronic camera such that the object is imaged on the electronic camera, by setting up a mean speckle diameter D greater than two pixels wide along at least one axis in the camera plane;

causing reference light and sample light to interfere on the camera, by configuring a path length profile and a phase gradient of the reference light along the predetermined axis in the camera plane, wherein the phase gradient has a contribution from the interval between $2\pi/D$ and $\pi/P$;

acquiring of a camera image, wherein the sample light scattered by a sectional face in the interior of the object and having the path length profile of the reference light contributes to interference patterns.

2. The method according to claim 1, characterized by displacing the path length profile of the reference beam with a time-dependent velocity and acquisition of further camera images, each at least indexed with a measure of the time-dependent displacement of the path length profile.

3. The method according to claim 2, characterized in that the path length profile of the reference beam is displaced continuously, wherein all path lengths vary by no more than a predetermined fraction of the central wavelength during an exposure time of the camera.

4. The method according to claim 1, characterized by separation of a camera image into a sectional image and a reflected image based on the phase gradient that is configured.

5. The method according to claim 4, wherein the separation of the camera image includes a two-dimensional Fourier filtering of the acquired camera image with respect to the phase gradient that is configured.

6. The method according to claim 4, characterized in that a three-dimensional model of the object is calculated from a plurality of differently indexed camera images by the sectional image values being assigned to a voxel array, taking into account the relative displacement of images of identical structures in differently indexed reflected images.

7. The method according to claim 1, characterized in that the light scattering object is the retina of a living eye.

8. The method according to claim 7, characterized in that the sectional face is a plane intersecting the cell layers of the retina at an angle.

9. The method according to claim 8, characterized by displacing the path length profile of the reference beam with a time-dependent velocity and acquisition of further camera images, each at least indexed with a measure of the time-dependent displacement of the path length profile and further characterized in that, from the relative displacement of the image of at least one layer boundary of the retina in differently indexed camera images, the change in the distance of the retina from the camera between the acquisition times of the camera images is inferred.

10. The method according to claim 7, characterized by displaying changes in the retina on the basis of the comparison of camera images and/or models with archived camera images and/or models of at least one previous acquisition time.

11. The method according to claim 7, characterized by biometric verification of the identity of a user.

12. An interferometer device for the exposure of a volume of a scattering object comprising:

a light source (1), which emits light with a coherence length of less than 25 microns and central wavelength $\lambda_0$;

a beam splitter (4) for dividing the light into a sample branch and reference branch;

means (5, 6) for changing the reference branch length;

means (9) for surface illumination of the object (10) in the sample branch;

an electronic camera (8) with pixels of width P;

a computing for processing the acquired camera an optical imaging system (7, 9) with numerical aperture NA and magnification M arranged for feeding the light scattered by the object (10) to the camera (8), wherein the optical imaging system is configured to image the object on the camera;

wherein the angle of incidence $\alpha$ of the light from the reference branch onto the camera is configured in accordance with the condition $\lambda_0/(2*P)>\sin(\alpha)>NA/(1.22*M)$.

13. The interferometer device according to claim 12, characterized in that the imaging optical system (7, 9) comprises an eccentric aperture diaphragm.

14. The interferometer device according to claim 12, characterized in that the computing unit is configured to calculate at least predetermined two-dimensional Fourier coefficients of the acquired camera images.

15. The interferometer device according claim 14, characterized in that the computing unit is designed to identify Fourier coefficients of acquired camera images in step with the image acquisition and to compare them with predetermined threshold values, and to send predetermined commands to the actuator controller on the basis of the comparison result.

16. The interferometer device according to claim 12, characterized in that it has an actuator drive acting on the means (5, 6) for changing the reference branch length and an actuator controller, wherein the actuator controller is communicatively connected to the computing unit for processing the acquired images.

* * * * *